(12) United States Patent  (10) Patent No.: US 7,641,669 B2
Roychowdhury et al.  (45) Date of Patent: *Jan. 5, 2010

(54) INTRAVASCULAR OCCLUSION BALLOON CATHETER

(75) Inventors: Suranjan Roychowdhury, Plymouth, MN (US); Katherine M. Prindle, Robbinsdale, MN (US); Kyle Eastenson, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1028 days.

This patent is subject to a terminal disclaimer.

(21) Appl. No.: 10/811,609

(22) Filed: Mar. 29, 2004

(65) Prior Publication Data

US 2004/0181189 A1  Sep. 16, 2004

Related U.S. Application Data

(63) Continuation of application No. 09/770,330, filed on Jan. 26, 2001, now Pat. No. 6,786,887.

(51) Int. Cl.
*A61M 29/00* (2006.01)
(52) U.S. Cl. ........................................ 606/192
(58) Field of Classification Search ............ 604/93, 604/96–99, 102, 915, 920, 921, 191–193; 606/194
See application file for complete search history.

(56) References Cited

U.S. PATENT DOCUMENTS

| | | | |
|---|---|---|---|
| 3,190,291 A | 6/1965 | Foley | |
| 3,331,371 A | 7/1967 | Rocchi et al. | |
| 3,378,011 A | 4/1968 | Vitello | |
| 3,379,197 A | 4/1968 | Hayes | |
| 3,402,717 A | 9/1968 | Doherty | |
| 3,402,718 A | 9/1968 | Doherty | |
| 3,417,750 A | 12/1968 | Carson | |
| 3,527,226 A | 9/1970 | Hakim | |
| 3,602,226 A | 8/1971 | Ericson | |
| 3,675,658 A | 7/1972 | Taylor | |
| 3,726,283 A | 4/1973 | Dye et al. | |
| 3,742,960 A | 7/1973 | Dye et al. | |
| 3,985,139 A | 10/1976 | Penar | |
| 4,318,410 A | 3/1982 | Chin | |
| 4,323,071 A | 4/1982 | Simpson et al. | |
| 4,411,055 A | 10/1983 | Simpson et al. | |
| 4,413,989 A | 11/1983 | Schjeldahl et al. | |
| 4,545,367 A | 10/1985 | Tucci | |
| 4,549,879 A | 10/1985 | Groshong et al. | |
| 4,564,014 A | 1/1986 | Fogarty et al. | |
| 4,582,181 A | 4/1986 | Samson | |

(Continued)

FOREIGN PATENT DOCUMENTS

DE    36 25 871 A1    2/1988

(Continued)

*Primary Examiner*—Manuel A Mendez
(74) *Attorney, Agent, or Firm*—Crompton, Seager & Tufte, LLC

(57) ABSTRACT

An intravascular occlusion balloon catheter having a removable hub, a profile sized to approximate a guidewire, and a means for venting air from the balloon. The removable hub and the small profile allow the occlusion balloon catheter to be used as a guidewire. The venting means allows air to be easily and reliably removed from the balloon prior to use.

21 Claims, 11 Drawing Sheets

U.S. PATENT DOCUMENTS

| | | | |
|---|---|---|---|
| 4,597,755 A | 7/1986 | Samson et al. |
| 4,606,347 A | 8/1986 | Fogarty et al. |
| 4,684,363 A | 8/1987 | Ari et al. |
| 4,715,378 A | 12/1987 | Pope, Jr. et al. |
| 4,748,982 A | 6/1988 | Horzewski et al. |
| 4,762,129 A | 8/1988 | Bonzel |
| 4,779,611 A | 10/1988 | Grooters et al. |
| 4,793,351 A | 12/1988 | Landman et al. |
| 4,811,737 A | 3/1989 | Rydell |
| 4,813,934 A | 3/1989 | Engelson et al. |
| 4,848,344 A | 7/1989 | Sos et al. |
| 4,930,341 A | 6/1990 | Euteneuer |
| 4,932,959 A | 6/1990 | Horzewski et al. |
| 4,943,278 A | 7/1990 | Euteneuer et al. |
| 4,998,923 A | 3/1991 | Samson et al. |
| 5,035,705 A | 7/1991 | Burns |
| 5,100,385 A | 3/1992 | Bromander |
| 5,114,398 A | 5/1992 | Trick et al. |
| 5,141,518 A | 8/1992 | Hess et al. |
| 5,180,364 A | 1/1993 | Ginsburg |
| 5,180,367 A | 1/1993 | Kontos et al. |
| 5,209,728 A | 5/1993 | Kraus et al. |
| 5,217,434 A | 6/1993 | Arney |
| 5,224,933 A | 7/1993 | Bromander |
| 5,246,420 A | 9/1993 | Kraus et al. |
| 5,324,263 A | 6/1994 | Kraus et al. |
| 5,334,153 A | 8/1994 | McIntyre et al. |
| 5,338,301 A | 8/1994 | Diaz |
| 5,378,238 A | 1/1995 | Peters et al. |
| 5,423,742 A | 6/1995 | Theron |
| 5,443,457 A | 8/1995 | Ginn et al. |
| RE35,176 E | 3/1996 | Powell |
| 5,695,468 A | 12/1997 | Lafontaine et al. |
| 5,743,875 A | 4/1998 | Sirhan et al. |
| 5,769,819 A | 6/1998 | Schwab et al. |
| 5,772,642 A | 6/1998 | Ciamacco, Jr. et al. |
| 5,776,099 A | 7/1998 | Tremulis |
| 5,785,685 A | 7/1998 | Kugler et al. |
| 5,807,328 A | 9/1998 | Briscoe |
| 5,814,016 A | 9/1998 | Valley et al. |
| 5,836,924 A | 11/1998 | Kelliher et al. |
| 5,916,194 A | 6/1999 | Jacobsen et al. |
| 6,017,323 A | 1/2000 | Chee |
| 6,071,273 A | 6/2000 | Euteneuer et al. |
| 6,102,931 A | 8/2000 | Thornton |
| 6,176,843 B1 | 1/2001 | DiCaprio et al. |
| 6,325,778 B1 * | 12/2001 | Zadno-Azizi et al. | 604/99.02 |
| 6,786,887 B2 * | 9/2004 | Roychowdhury et al. | 604/96.01 |

FOREIGN PATENT DOCUMENTS

| | | |
|---|---|---|
| GB | 2 209 121 A | 5/1989 |
| WO | WO 93/17750 | 9/1993 |

\* cited by examiner

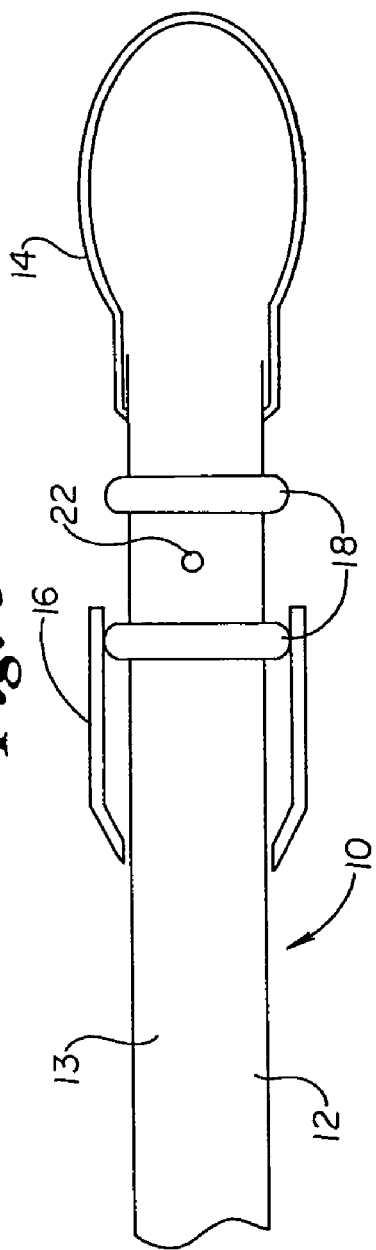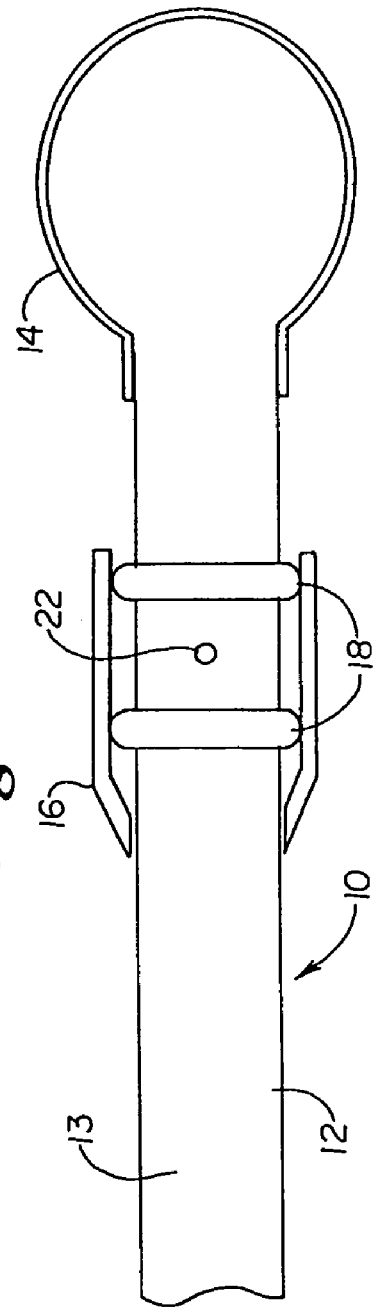

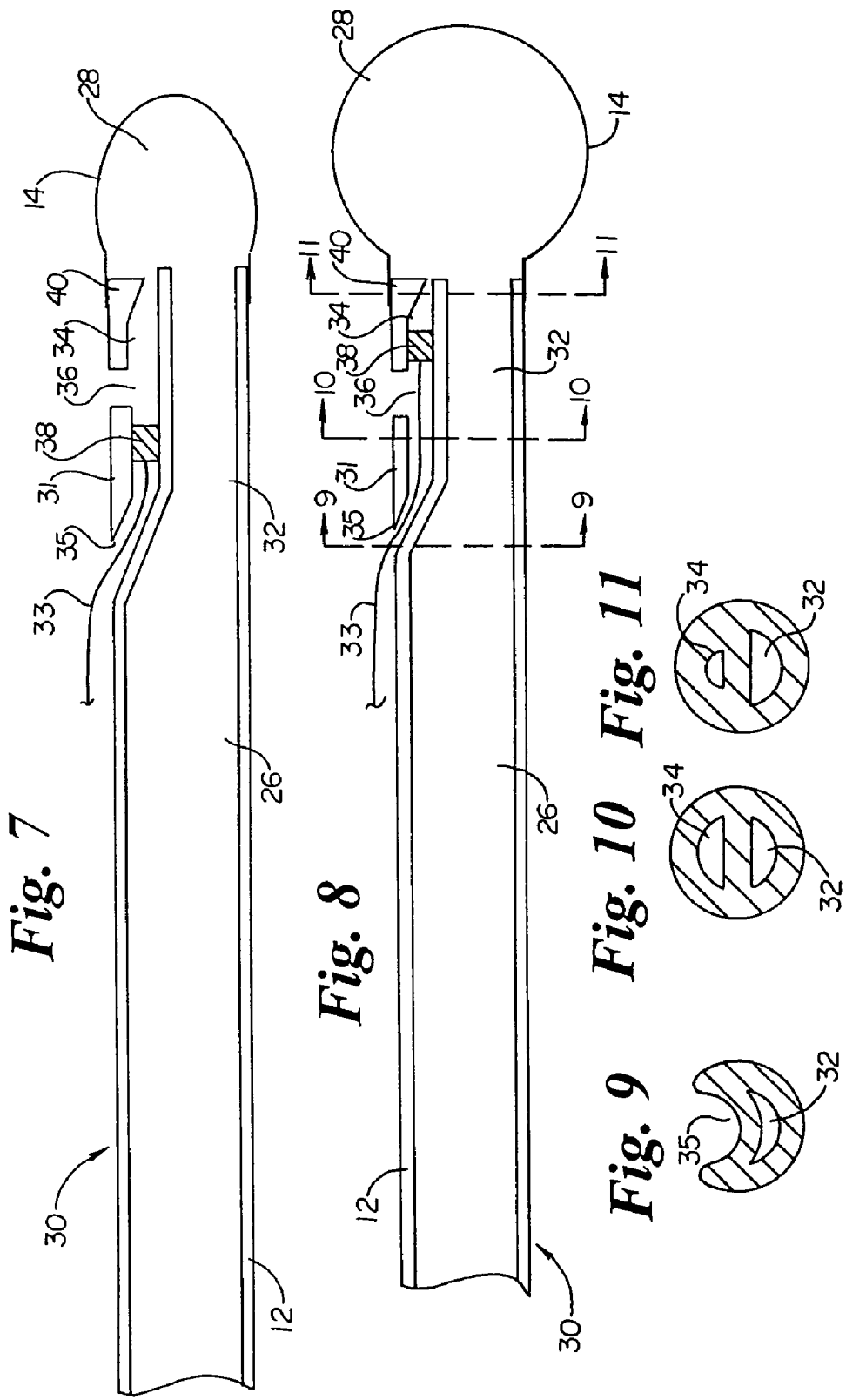

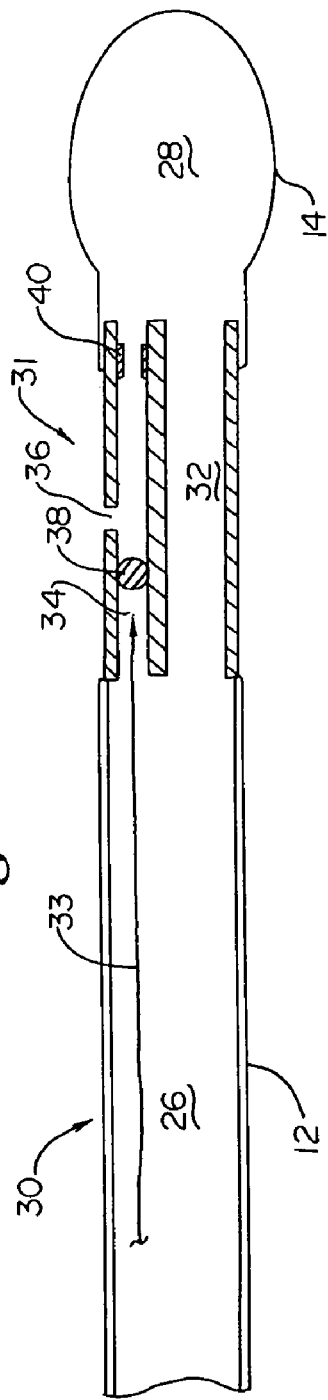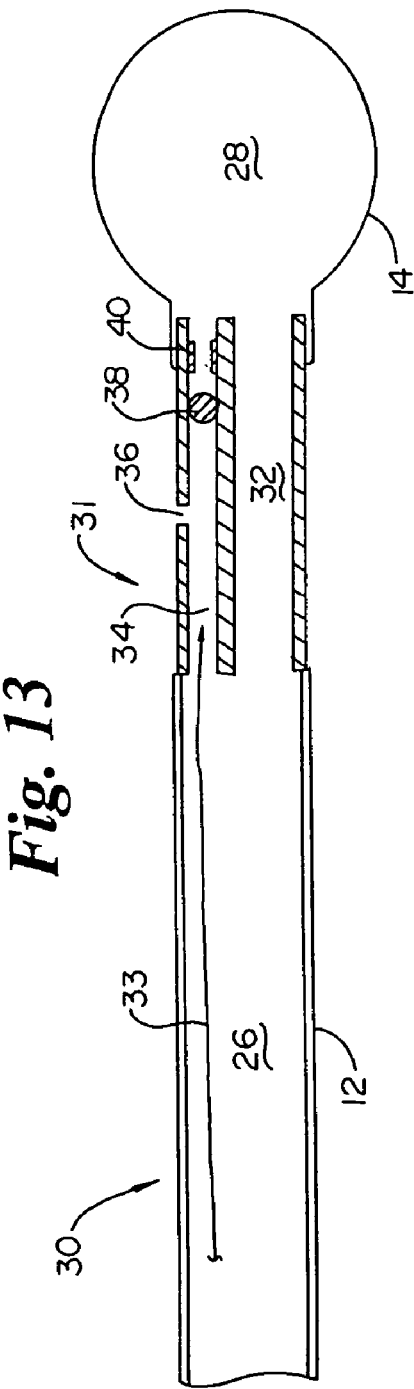

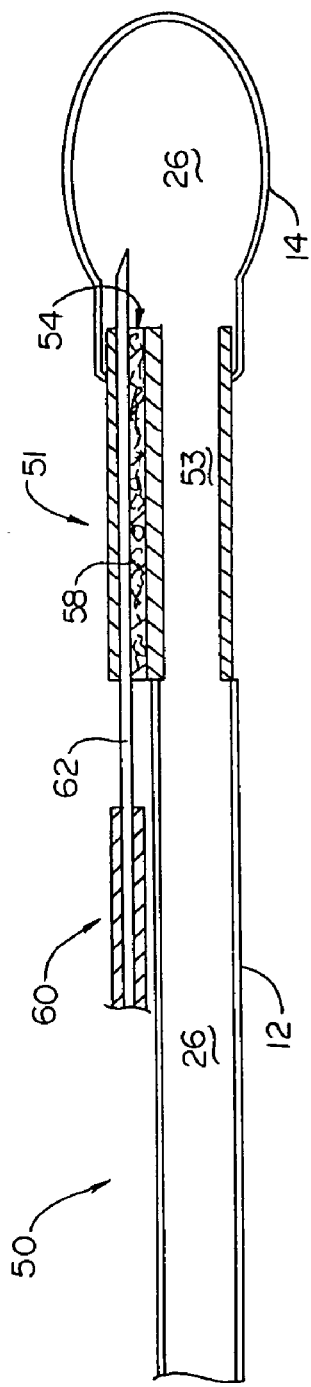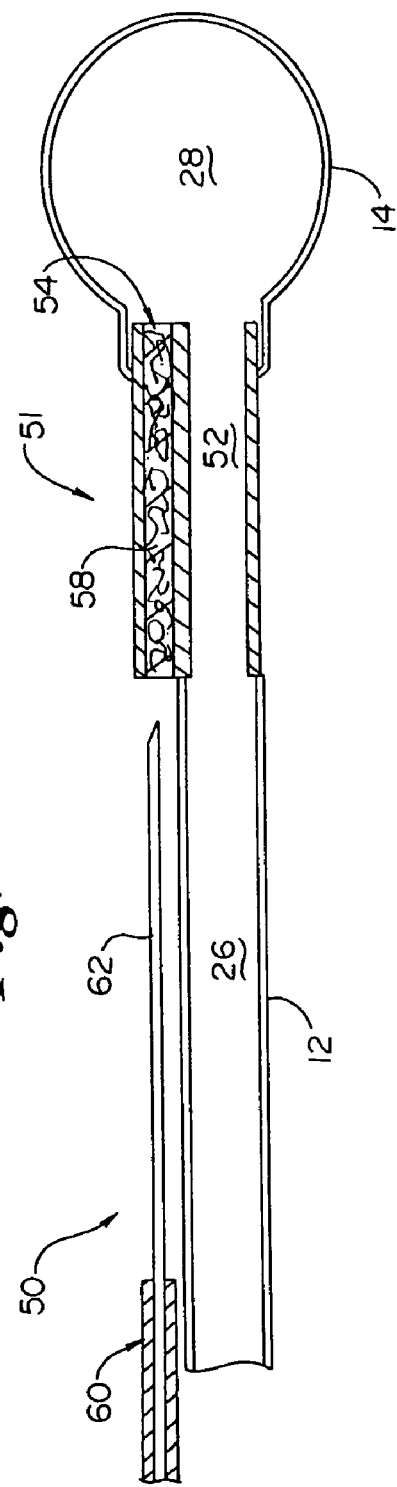

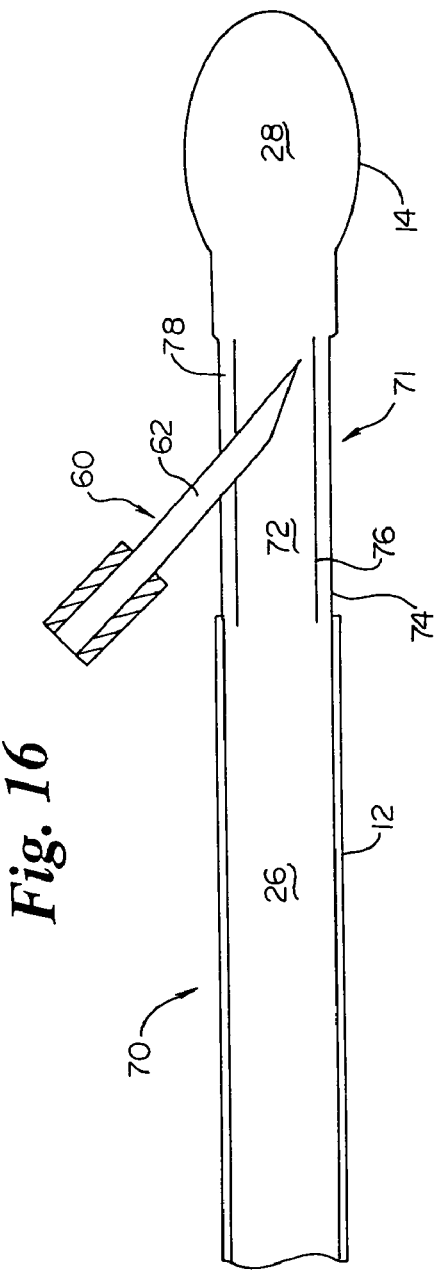
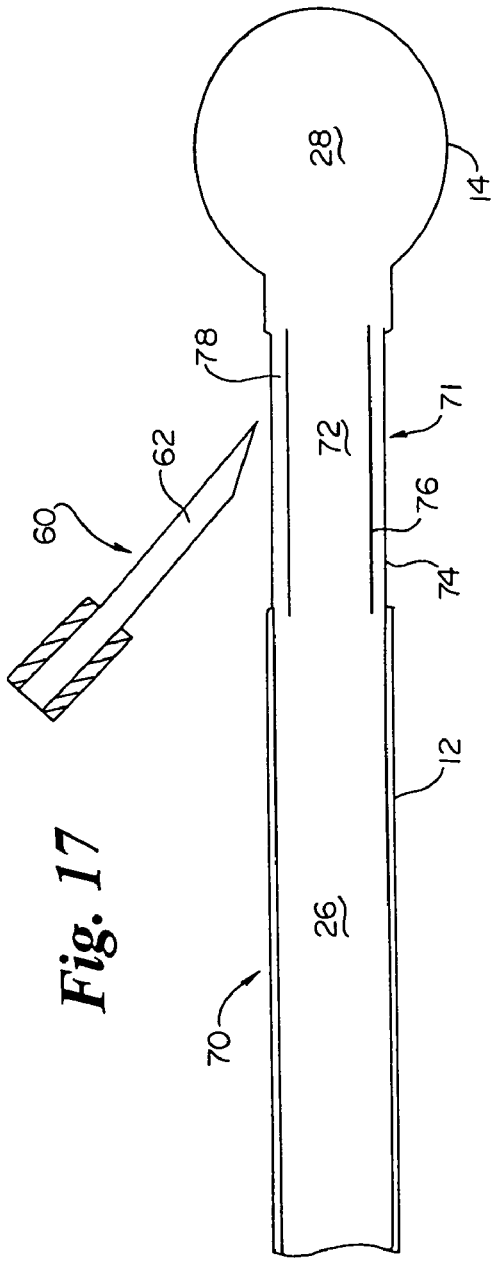

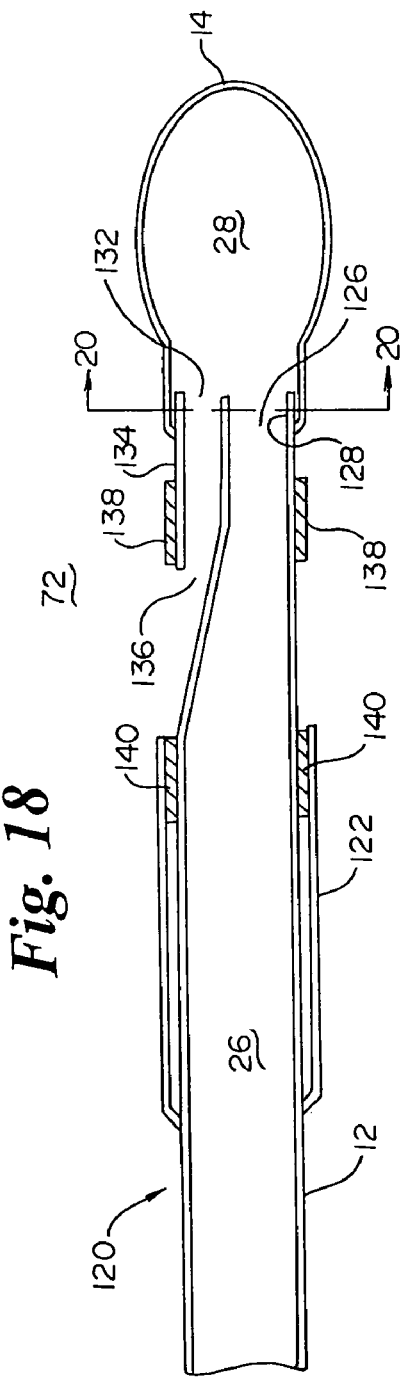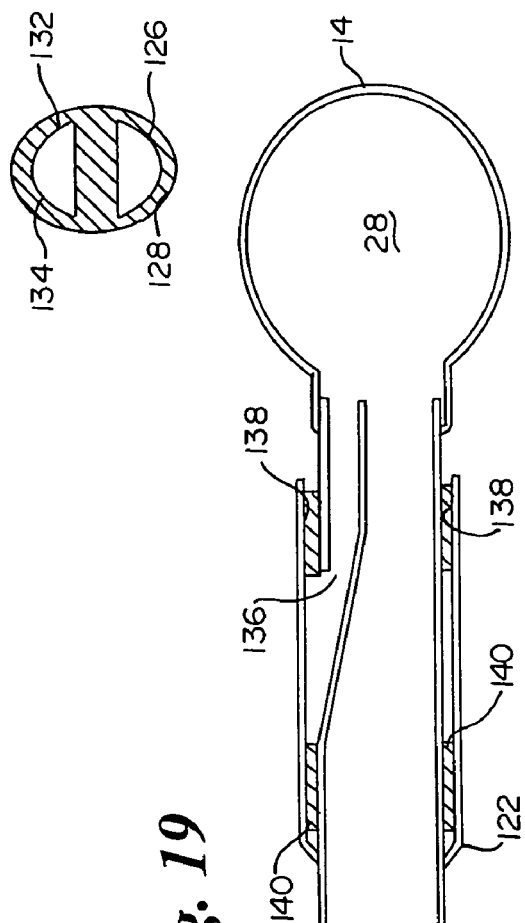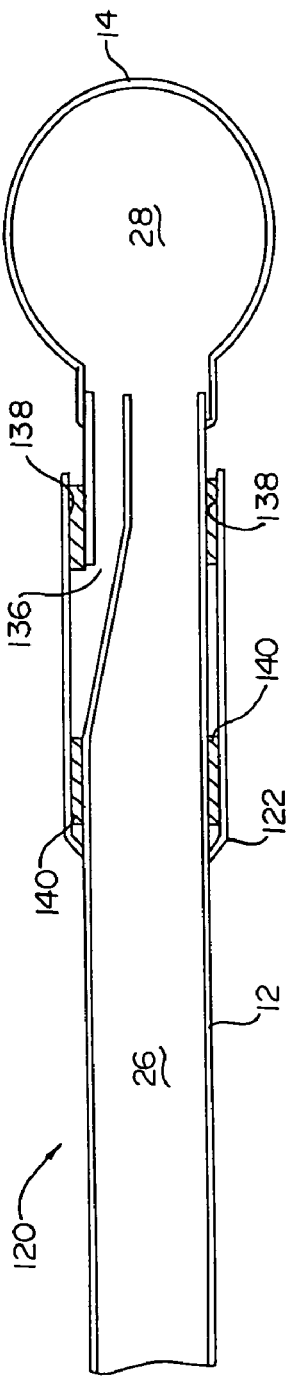

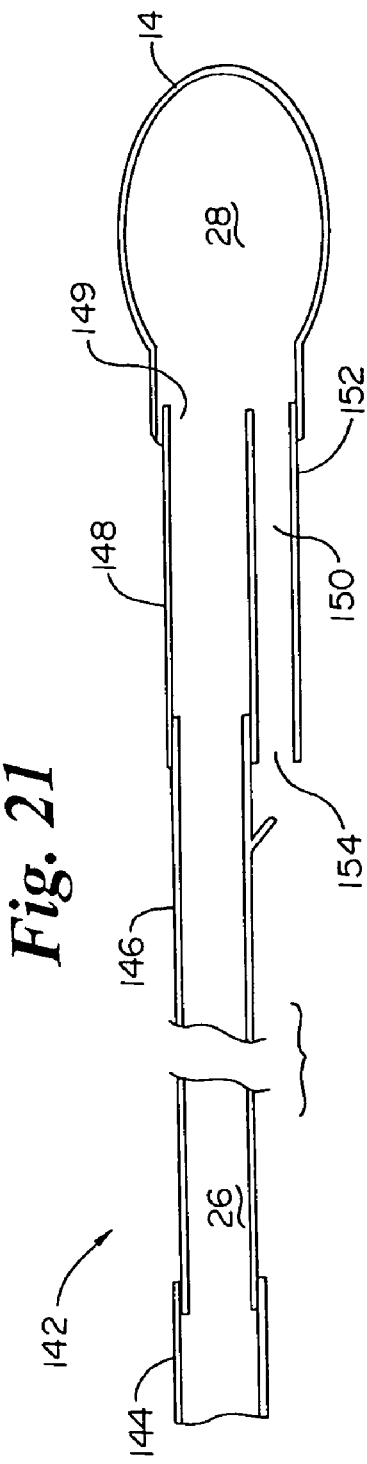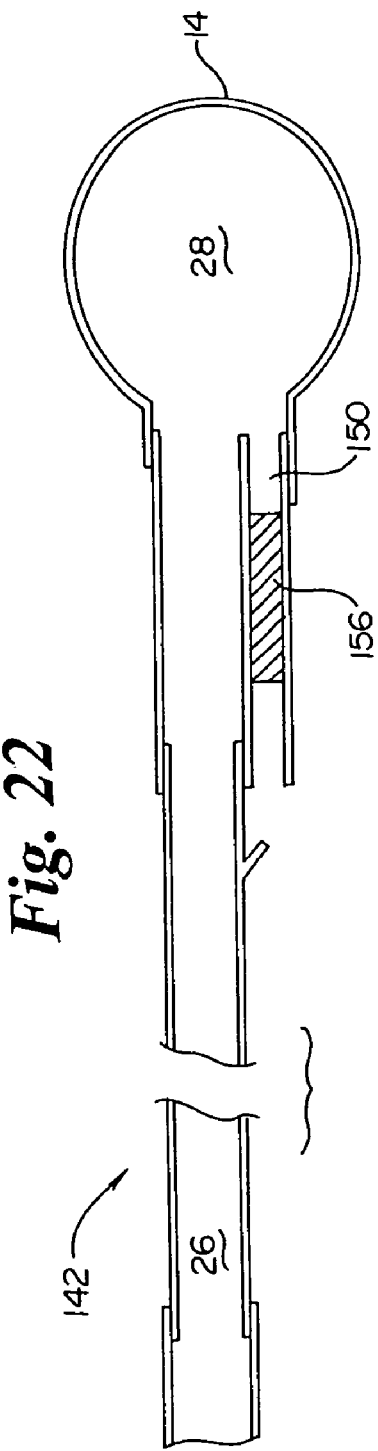

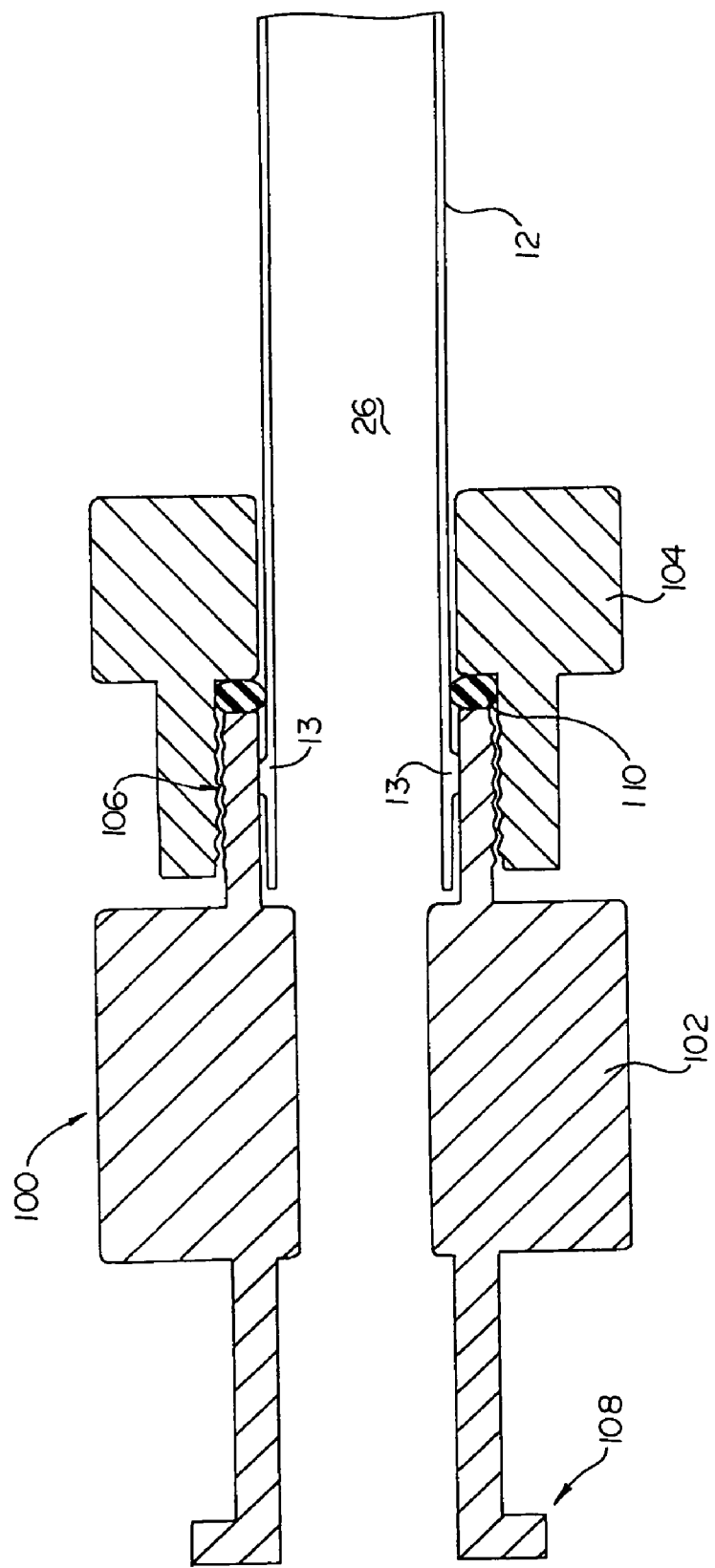

ized are approximately 140 300 cm or more in length. An occlusion catheter of such length may compromise the ability of the treating physician to manipulate the catheter and is otherwise cum bersome to handle. Accordingly, it is desirable to provide a relatively short intravascular occlusion balloon adapted for use with a standard length primary catheter. It is also desirable to provide an occlusion catheter that is simple to prepare for use.

INTRAVASCULAR OCCLUSION BALLOON CATHETER

This application is a continuation of U.S. Ser. No. 09/770,330, filed Jan. 26, 2001, now U.S. Pat. No. 6,786,887.

FIELD OF THE INVENTION

The present invention generally relates to intravascular devices and methods of use. In particular, the present invention relates to intravascular occlusion balloon catheters and their use to prevent migration of embolic materials during an intravascular procedure.

BACKGROUND OF THE INVENTION

Minimally invasive intravascular procedures are common in the treatment of vascular disease. For example, intravascular restrictions due to atherosclerosis, restenosis, or the like may be dilated by intravascular balloon catheters or may be removed by intravascular atherectomy catheters. These intravascular procedures and the use of their associated devices may result in embolic particles being dislodged as the restriction is being dilated or cut. The embolic particles may cause an embolism to form downstream of the restriction which, in turn, may compromise the flow of blood to the surrounding tissue.

To alleviate this potential risk, intravascular occlusion balloon catheters have been developed. Such occlusion catheters typically include an elongate shaft and a distally mounted balloon. The shaft and the balloon are insertable into a lumen of a primary catheter such as a dilatation catheter or an atherectomy catheter. The occlusion balloon is positioned distal of the treatment site and temporarily inflated to prevent embolic particles from flowing downstream as the restriction is being dilated or cut. After the restriction has been treated, the primary catheter is removed over the occlusion balloon catheter. The treatment site proximal of the occlusion balloon is then aspirated through a guide catheter. Once the embolic particles have been aspirated, the occlusion balloon is deflated and removed from the patient.

In order to retract the primary catheter over the occlusion balloon catheter, the occlusion catheter must be approximately two times the length of the guidewire lumen of the primary catheter. Dilatation catheters are typically 70-150 cm in length, which requires the occlusion catheter to be approximately 140-300 cm or more in length. An occlusion catheter of such length may compromise the ability of the treating physician to manipulate the catheter and is otherwise cumbersome to handle. Accordingly, it is desirable to provide a relatively short intravascular occlusion balloon adapted for use with a standard length primary catheter. It is also desirable to provide an occlusion catheter that is simple to prepare for use.

SUMMARY OF THE INVENTION

The present invention provides an intravascular occlusion balloon catheter having a length slightly greater than a conventional balloon or atherectomy catheter. The intravascular occlusion balloon catheter includes, in preferred embodiments, a removable hub, a profile sized to approximate a guidewire, and a means for venting air from the balloon. The removable hub and the small profile allow the occlusion balloon catheter to be used as a standard length guidewire. The venting means allows air to be easily and reliably removed from the balloon prior to use.

The venting means may comprise an annular ring disposed about the distal end of the shaft with an intermediate tube fixedly connected to the balloon and movably disposed about the annular ring. The intermediate tube and the annular ring form a fluid tight seal to permit inflation and deflation of the balloon. The intermediate tube includes a vent hole, wherein a vent path is opened through the tube and the vent hole when the hole is positioned distal of the annular ring. The vent path may be closed to inflate the balloon by positioning the hole proximal of the annular ring.

In one alternative embodiment, a pair of longitudinally spaced annular rings are included proximate the distal end of the shaft with at least one hole penetrating through the shaft between the annular rings. The shaft extends distally from the more distal annular ring and the balloon is sealingly affixed at the distal end thereof. An intermediate tube is slidably mounted relative to the longitudinally spaced annular rings such that in a first position or proximal position, the vent hole is opened through the tube and a vent path is created to the exterior of the catheter for purging the catheter. In a second position or distal position, the intermediate tube extends over both the proximal and distal annular rings in sealing engagement to block the vent hole to allow inflation of the balloon during use.

Alternatively, the venting means may comprise an intermediate tube disposed between the balloon and the distal end of the shaft. The tube includes an inflation lumen, a vent lumen, and a vent hole, with a movable plug disposed in the vent lumen. A vent path is opened through the vent lumen and the vent hole when the plug is positioned proximal of the hole. The vent path may be closed to inflate the balloon by positioning the plug distal of the hole. A retainer may be disposed in the vent lumen distal of the vent hole to prevent the plug from entering the balloon. In this embodiment, a pusher is used to move the plug from a venting configuration to an inflation configuration. The catheter shaft may include an access port proximal of the movable plug so that the pusher may be inserted through such port. This design eliminates the need for the pusher to extend through the inflation lumen of the shaft. However, an alternative design includes the pusher extending within the inflation lumen to the movable plug.

The venting means may also comprise a re-sealable material disposed in a lumen of an intermediate tube disposed between the balloon and the distal end of the shaft. A vent path is opened when a needle is disposed through the re-sealable material. The vent path may be closed to inflate the balloon by removing the needle from the re-sealable material.

The venting means may also comprise a vent lumen extending between the balloon interior and a vent hole. A coaxially disposed intermediate tube or sleeve may be slidably disposed over the catheter shaft in a first position to allow venting through the vent hole. The slidably disposed sleeve may be moved to a second, sealed, position for occluding the vent hole to allow inflation of the balloon.

The venting means may also comprise a vent lumen extending between the balloon interior and the vent hole together with a plug dimensioned for insertion into the vent lumen. The catheter can be purged through the vent lumen, followed by plugging the vent lumen by inserting the plug. The plug may be radiopaque and may comprise a swellable polymer injected into the vent lumen.

The venting means may also comprise a vent lumen extending between the balloon interior, a vent hole, and a proximally disposed plug access hole vent. A plug may be slidably disposed in the vent lumen in a first position proximal of the vent hole for purging the balloon. The plug may be moved into a second position for occluding the vent hole for inflating the balloon. The plug may be pushed distally into position over the vent hole using a push rod inserted through the plug access hole.

The present invention also includes a method of using an intravascular occlusion balloon catheter having a removable hub in combination with a primary intravascular catheter having a guidewire lumen. In addition, the occlusion balloon catheter may have a venting mechanism, such that air may be vented from the balloon prior to intravascular insertion.

BRIEF DESCRIPTION OF THE DRAWINGS

FIG. 5 is a plan view of an alternative distal portion of an occlusion balloon catheter, shown in a venting state;

FIG. 6 is a plan view of the occlusion balloon catheter illustrated in FIG. 5, but shown in an inflated state having a vent hole sealed by an intermediate tubular member;

FIG. 7 is a partial longitudinal cross-sectional view of a distal portion of an occlusion balloon catheter, shown in a deflated venting state, and incorporating a push rod and plug arrangement accessible from exterior of the catheter shaft;

FIG. 8 is a partial longitudinal cross-sectional view of a distal portion of the occlusion balloon catheter of FIG. 7 depicting the movable plug positioned to seal the catheter for inflation of the balloon;

FIG. 9 is a cross-sectional view of the shaft of the occlusion balloon catheter of FIG. 8 taken at line 9-9;

FIG. 10 is a cross-sectional view of the shaft of the occlusion balloon catheter of FIG. 8 taken at line 10-10;

FIG. 11 is a cross-sectional view of the shaft of the occlusion balloon catheter of FIG. 8 taken at line 11-11;

FIG. 12 is a partial longitudinal cross-sectional view of a distal portion of an occlusion balloon catheter, shown in a deflated venting state, in accordance with another embodiment of the present invention;

FIG. 13 is a partial longitudinal cross-sectional view of the occlusion balloon catheter illustrated in FIG. 12, but shown in an inflated state;

FIG. 14 is a partial longitudinal cross-sectional view of a distal portion of an occlusion balloon catheter, shown in a deflated state, in accordance with yet another embodiment of the present invention;

FIG. 15 is a partial longitudinal cross-sectional view of the occlusion balloon catheter illustrated in FIG. 14, but shown in an inflated state;

FIG. 16 is a longitudinal plan view of a distal portion of an occlusion balloon catheter, shown in a deflated state, in accordance with a further embodiment of the present invention;

FIG. 17 is a longitudinal plan view of the occlusion balloon catheter illustrated in FIG. 16, but shown in an inflated state;

FIG. 18 is a partial longitudinal cross-sectional view of an occlusion balloon catheter having a distal purge lumen, exit port, and coaxially disposed slidable sleeve for sealing the exit port shown in an open position;

FIG. 19 is a partial longitudinal cross-sectional view of the occlusion balloon catheter illustrated in FIG. 18, shown in a closed position;

FIG. 20 is a transverse, cross-sectional view through 20-20 of FIG. 18, illustrating one set of lumen shapes;

FIG. 21 is a partial longitudinal cross-sectional view of an occlusion balloon catheter having a distal purge lumen, and exit port shown in an open configuration;

FIG. 22 is a longitudinal cross-sectional view of the occlusion balloon catheter illustrated in FIG. 21 having the distal purge lumen sealed with a plug;

FIG. 25 is a longitudinal cross-sectional view of a removable hub disposed on a proximal shaft in accordance with the present invention.

DETAILED DESCRIPTION OF THE DRAWINGS

The following detailed description should be read with reference to the drawings in which similar elements in different drawings are numbered the same. The drawings, which are not necessarily to scale, depict selected preferred embodiments and are not intended to limit the scope or spirit of the invention.

Figure 1:
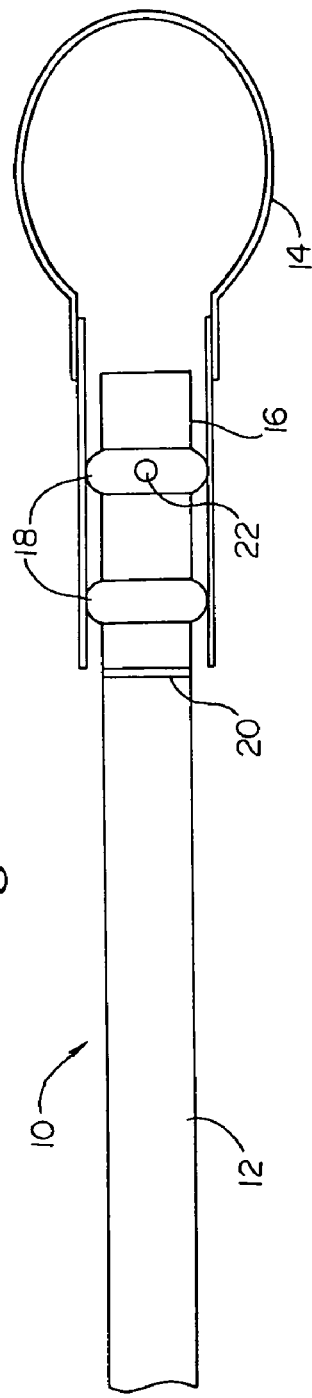
FIG. 1 is a plan view of a distal portion of an occlusion balloon catheter, shown in an inflated state, in accordance with one embodiment of the present invention.
Figure 2:
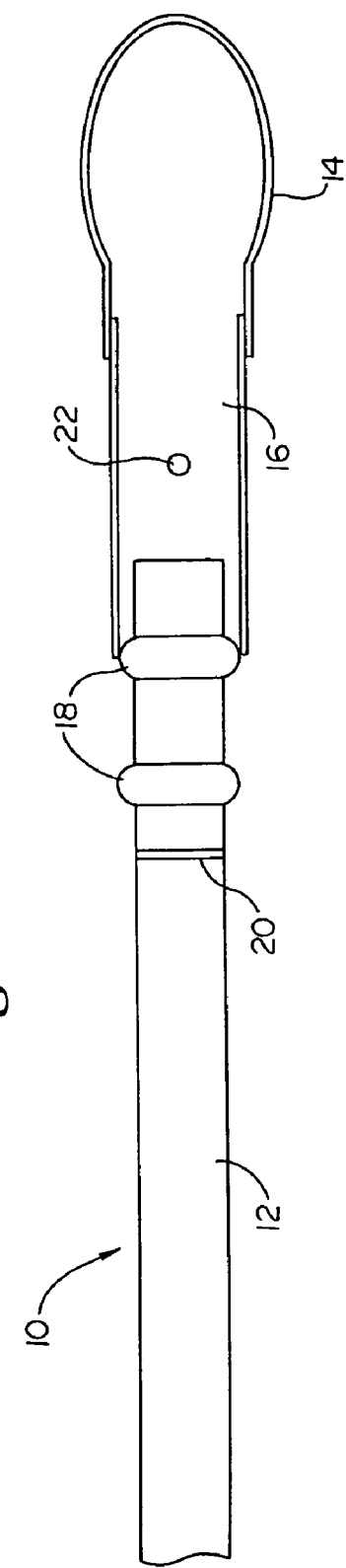
FIG. 2 is a plan view of the occlusion balloon catheter illustrated in FIG. 1, but shown in a deflated venting state.

Refer now to FIGS. 1 and 2, which illustrate plan views of a distal portion of an occlusion balloon catheter 10 in accordance with one embodiment of the present invention. Occlusion balloon catheter 10 includes an elongate shaft 12 and a distally mounted occlusion balloon 14. In FIG. 1, the balloon 14 is shown in an inflated state, and in FIG. 2, the balloon 14 is shown in a deflated state.

Occlusion balloon catheter 10 also includes an intermediate tube 16 fixedly and sealably connected to the proximal end of the balloon 14. The intermediate tube 16 is coaxially disposed about the distal end of the shaft 12 and is movable relative thereto. Both the intermediate tube 16 and the occlusion balloon 14 are shown as being transparent in order to clearly illustrate the arrangement of parts at the distal portion of the catheter 10.

One or more annular ring(s) 18 are disposed proximate the distal end of the elongate shaft 12 to form a seal with the inside surface of the intermediate tube 16 during longitudinal movement or at various fixed longitudinal portions of intermediate tube 16. Preferably, two annular ring(s) 18 are provided to ensure a fluid-tight seal between the shaft 12 and the intermediate tube 16. With this arrangement, the balloon 14 and the intermediate tube 16 may be moved in the longitudinal direction relative to the elongate shaft 12 while maintaining a fluid seal therebetween.

Intermediate tube 16 also includes a vent hole 22 positioned adjacent to or proximal of the annular ring(s) 18. A shaft marker 20 is provided on the distal end of the elongate shaft 12 to indicate that the vent hole 22 is properly positioned. The vent hole 22 is sealed in this position to close the vent path and define an inflation path. The inflation path is defined through the lumen 26 (not visible) of the elongate shaft 12 to the interior 28 (not visible) of the inflatable balloon 14. Accordingly, the balloon 14 may be inflated by connecting a fluid source (not shown) to a removable hub 100 (illustrated in FIG. 25) connected to the proximal end of the elongate shaft 12.

The movable seal between the annular ring(s) 18 and the inside surface of the intermediate tube 16 allows the intermediate tube 16 and the balloon 14 rigidly connected thereto to be slid in a distal direction such that the vent hole 22 is positioned distal of the annular ring(s) 18, as illustrated in FIG. 2. With the vent hole 22 positioned distal of the annular ring(s) 18, the catheter 10 is now ready for purging air from the interior 26 of the catheter 10, and particularly from the interior 28 of the balloon 14. Air may be purged via a vent pathway defined from the lumen of the shaft, into the interior 28 of the balloon 14, through the annular space between the intermediate tube 16 and the shaft 12, up to the annular ring(s) 18, and out the vent hole 22.

To vent the air from the catheter 10, the removable hub 100 (see FIG. 25) is connected to the proximal end of the elongate shaft 12. A pressurized fluid source such as a syringe or inflation device containing a suitable inflation medium such as water or saline is connected to the removable hub 100. Fluid is injected into the catheter 10 using the pressurized fluid source connected to the removable hub 100 until fluid begins to emerge from the vent hole 22. In order to ensure that the inflation medium has displaced all of the air in the balloon 14, the flow of pressurized inflation medium is continued until a steady stream of liquid emerges from the vent hole 22. Preferably, a steady stream of liquid is allowed to flow from the vent hole 22 for approximately 15 to 20 seconds. The intermediate tube 16 and the balloon 14 are then slid proximally until the proximal end of the intermediate tube 16 is in alignment with the shaft marker 20. With the proximal end of the intermediate tube 16 aligned with the shaft marker 20, the vent hole 22 is positioned adjacent to or proximal of the annular ring(s) 18 to thereby close the vent pathway. The occlusion balloon catheter 10 is now prepared for intravascular use.

In use, the occlusion balloon catheter 10 may be inserted before, after, or simultaneously with the primary treatment catheter (i.e., a balloon dilatation catheter or an atherectomy device). If the occlusion catheter 10 is to be inserted after the primary catheter has been inserted into the vascular system, or if the occlusion catheter 10 is to be inserted at the same time as the primary catheter, it is not necessary to initially remove the hub 100 from the proximal end of the shaft 12. If the occlusion catheter 10 is inserted into the vascular system prior to the primary catheter, it is necessary to initially remove the hub 100 such that the primary catheter may be advanced over the occlusion catheter 10.

Regardless of order, once the occlusion balloon 14 has been inflated in the desired vascular position, a mandrel may be inserted into the proximal end of the elongate shaft 12 to occlude the inflation lumen 26. The mandrel, (not shown) is sized to form an interference fit with the inside surface of the elongate shaft 12 to form a fluid tight seal and thereby occlude the inflation lumen 26. The mandrel is also sized to be equal to or less than the profile of the catheter 10, such that it does not interfere with the advancement or removal of the primary catheter. Once the proximal end of the inflation lumen 26 has been occluded by the mandrel, the hub 100 may be removed from the proximal end of the shaft 12.

After treatment, the primary catheter may be removed from the occlusion catheter 10, which is held in place by the occlusion balloon 14 engaging the inside wall of the vessel. The treatment site may then be aspirated in the conventional manner using a guide catheter through which both the primary catheter and the occlusion catheter 10 have been inserted. After aspiration, the mandrel may be removed from the shaft 12 to deflate the balloon 14. After deflation of the balloon 14, the occlusion catheter 10 may be removed from the patient's vascular system.

The occlusion balloon catheter 10 may have a length slightly greater than the primary catheter and an outside profile approximating a conventional guidewire, such that the catheter 10 may be inserted into the guidewire lumen of the primary catheter. For example, the occlusion balloon catheter 10 may have a length of approximately 150 cm and an outside profile of approximately 0.035 inches when in a deflated state. Those skilled in the art will recognize that the dimensions of the catheter 10 may be modified to be compatible with a wide variety of primary catheters depending on the length and guidewire lumen diameter of the chosen primary catheter.

Figure 3:
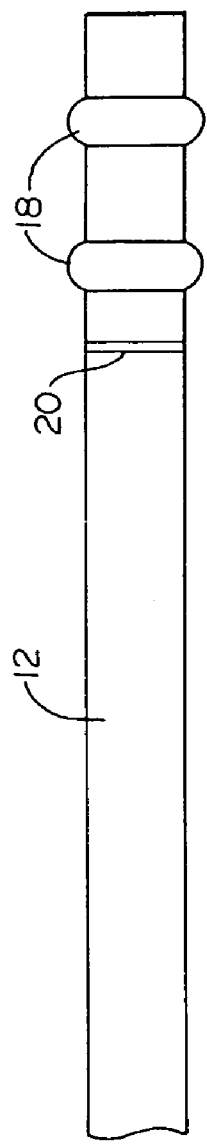
FIG. 3 is a plan view of the shaft of the occlusion balloon catheter illustrated in FIG. 1.
Figure 4:
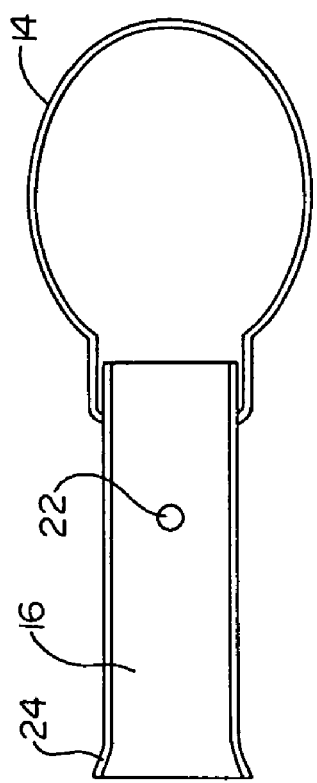
FIG. 4 is a plan view of the balloon and intermediate tube of the occlusion balloon catheter illustrated in FIG. 1.

FIGS. 3 and 4 are detailed views of the shaft 12, the intermediate tube 16, and the balloon 14 of the occlusion balloon catheter 10 illustrated in FIGS. 1 and 2. The elongate shaft 12 may be approximately 150 cm long and may be formed of a suitable medical grade material to approximate the characteristics of a similarly dimensioned guidewire. The annular ring (s) 18 may be formed of a medical grade adhesive, such as a cyanolacrolate available under the tradename LOCTITE Part No. 3301. The annular ring(s) 18 may be spaced about 0.260 inches apart, with the distal annular ring 18 spaced about 0.668 inches from the distal end of the shaft 12. The shaft marker 20 may be located approximately 0.979 inches from the distal end of the shaft 12, but may be varied depending on the length of the intermediate tube 16 and the position of the vent hole 22.

The intermediate tube 16 may be formed of a suitable medical grade material having a length of approximately 1.30 inches. The proximal end 24 of the intermediate tube 16 may be flared to provide easy insertion of the shaft 12 therein. The vent hole 22 may be positioned 0.300 inches from the proximal end of the intermediate tube 16 and may have an inside diameter of approximately 0.016 inches.

Referring now to FIGS. 5 and 6, plan views of an alternative portion of an occlusion balloon catheter 10 similar to that which is depicted in FIGS. 1 and 2, are illustrated. Except as described herein, the structure and use of occlusion balloon catheter 10 of FIGS. 5 and 6 is the same as catheter 10 described with reference to FIGS. 1-4. Occlusion balloon catheter 10 includes an elongate shaft 12 which has a balloon 14 fixedly secured proximate its distal end and extending distal thereto. The lumen 13 of shaft 12 is utilized for injecting inflation fluid into the balloon 14.

The shaft 12 includes at least two annular rings 18 disposed proximal of the balloon 14 and extending around the circumference of the shaft 12. The annular rings 18 are spaced longitudinally, and at least one vent hole 22 penetrates from outside the shaft 12 into the lumen 13.

An intermediate tube 16 is coaxially disposed in longitudinally movable relation to the shaft 12 proximate the annular rings 18. As depicted in FIG. 5, the intermediate tube 16 may be located in a first longitudinal position such that vent hole 22 is open to the outside of the shaft to allow venting of air from within. In this way, the shaft 12 may be purged before intravascular use. Further, as depicted in FIG. 6, the intermediate tube 16 may be moved to a second longitudinal position such that the interior surface of the intermediate tube 16 engages both annular rings in sealing arrangement. This arrangement blocks the vent hole 22 and allows inflation of balloon 14 through lumen 13 of shaft 12.

Refer now to FIGS. 7 and 8 which illustrate a partial longitudinal cross-sectional view of a distal portion of an occlusion balloon catheter 30 in accordance with an alternative embodiment of the present invention. Except as described herein, the structure and use of occlusion balloon catheter 30 is the same as the occlusion balloon catheter 10 described with reference to FIGS. 1-6. The depicted embodiment includes an elongate shaft 12 and a balloon 14 mounted on the distal end of the shaft 12. A distal portion of the shaft 12 includes an intermediate tube or tubular portion 31 of shaft 12 which is disposed between the proximal portion of elongate shaft 12 and the balloon 14. In alternative embodiments of the present invention, the intermediate tube or tubular portion 31 may be a separate tube which is connected to the distal end of the proximal portion of the elongate shaft 12, or it may be an integral portion which is formed at the time of manufacture of the elongate shaft 12. In a preferred embodiment, the intermediate tube 31 is thermally bonded to the distal end of the proximal portion of elongate shaft 12.

Intermediate tube 31 includes an inflation lumen 32, which provides fluid communication between the inflation lumen 26 of the shaft 12 and the interior 28 of the balloon 14. The intermediate tube 31 also includes a vent lumen 34 which includes a vent hole 36 opening to the exterior of the intermediate tube 31. As illustrated in the cross-sections of FIGS. 9-11, intermediate tube 31 is preferably a dual-lumen extrusion having side-by-side lumens 32 and 34. It is, however, recognized that intermediate tube 31 may be formed by other suitable means, such as two separate extruded tubes arranged side-by-side and connected by adhesive, or the like.

The embodiment of FIGS. 7 and 8 further includes a pusher or push rod 33 which is insertable through a side access port into the vent lumen 34 of intermediate tube 31. A movable plug 38 is disposed in the vent lumen 34 to provide a fluid-tight seal when positioned distal of the vent hole 36 as depicted in FIG. 8. The push rod or pusher 33 is utilized to move the movable plug 38 from a first position which is proximal of the vent hole 36 to a position distal of the vent hole 36 in sealing arrangement with the lumen wall 34. In the first position, air may be purged from the shaft 12 and balloon 14, while in the second position, the balloon may be inflated during intravascular use. A retainer 40 disposed in the vent lumen 34 provides a reduction in the size of lumen 34 and prevents the removable plug 38 from entering the interior 28 of the balloon 14, thereby retaining the removal of plug 38 in the vent lumen 34. Although the embodiment of FIGS. 7 and 8 depict a separate vent hole 36 and access port 35 for the pusher 33, it is recognized that a single port could provide both functions provided the movable plug 38 is sized for sealing engagement with the lumen wall at a reduced diameter longitudinal location, while allowing flow of air and fluid during purging when positioned proximally in a larger diameter portion of the lumen which allows flow around the movable plug.

Refer now to FIGS. 12 and 13, which illustrate longitudinal cross-sectional views of a distal portion of an occlusion balloon catheter 30 in accordance with another embodiment of the present invention. Except as described herein, the structure and use of occlusion balloon catheter 30 is the same as occlusion catheter 10 described with reference to FIGS. 1-6 or occlusion catheter 30 described with reference to FIGS. 7-8. Occlusion balloon catheter 30 includes an intermediate tube or tubular portion 31 disposed between the elongate shaft 12 and the balloon 14 which may be a separate tubular member or formed integral with shaft 12. The proximal end of the intermediate tube 31 is connected to the distal end of the elongate shaft 12, and the proximal end of the balloon 14 is connected to the distal end of the intermediate tube 31.

The intermediate tube 31 includes an inflation lumen 32, which provides fluid communication between the inflation lumen 26 of the shaft 12 and the interior 28 of the balloon 14. The intermediate tube 31 also includes a vent lumen 34 and a vent hole 36. As illustrated, intermediate tube 31 is a dual-lumen extrusion having side-by-side lumens 32 and 34. Those skilled in the art, however, will recognize that the intermediate tube 31 may be formed by other suitable means, such as two separately extruded tubes arranged side-by-side and connected by adhesive, or the like.

A movable plug 38 is disposed in the vent lumen 34 to provide a fluid-tight seal therein. The intermediate tube also includes a retainer 40 disposed in the vent lumen 34 adjacent the distal end of the tube 31. Retainer 40 prevents the removable plug 38 from entering the interior 28 of the balloon 14, thereby maintaining the removable plug 38 in the vent lumen 34. As depicted, a pusher or push rod 33 may be disposed with the shaft lumen 26 to contact and reposition removable plug 38 as necessary between a purge position and a balloon inflation position.

With the movable plug 38 positioned proximal of the vent hole 36, a vent pathway is defined extending from the interior 28 of the balloon 14, through the vent lumen 34 of intermediate tube 31, and out the vent hole 36. In this manner, air in the catheter 30, and in particular the interior 28 of the balloon 14, may be purged or vented as described previously. Once the air has been displaced from the interior of the catheter 30, the plug 38 may be advanced in the distal direction through the vent lumen 34. When the movable plug 38 is in a position distal of the vent hole 36, the vent pathway is sealed.

The movable plug 38 may be advanced distal of the vent hole 36 by utilizing the push rod 33 inserted into the proximal end of the catheter 30, through the inflation lumen 26, and into the vent lumen 34 of the intermediate tube 31. Such a push rod should be dimensioned at the distal end thereof to be insertable into the vent lumen 34. Once the movable plug 38 is in the desired position, the push rod may be removed. The occlusion catheter 30 is then ready for use.

Refer now to FIGS. 14 and 15, which illustrate a longitudinal cross-sectional view of a distal portion of an occlusion balloon catheter 50 in accordance with yet another embodiment of the present invention. Except as described herein, the structure and use of occlusion catheter 50 is the same as occlusion catheter 10 discussed with reference to FIGS. 1-6 and the occlusion catheter 30 discussed with reference to FIGS. 7-13. Occlusion balloon catheter 50 includes an intermediate tube 51 disposed between the elongate shaft 12 and the inflatable balloon 14. The intermediate tube 51 includes an inflation lumen 52 fluidly connecting the inflation lumen 26 of the shaft 12 to the interior 28 of the balloon 14.

The intermediate tube 51 also includes a vent lumen 54 having a resealable material 58 disposed therein. The resealable material 58, such as a medical grade silicone, may be pierced by a needle 60 or other similar structure to define a vent pathway from the interior of the balloon 28. Specifically, a vent pathway is defined from the interior 28 of the balloon 14 through the lumen 62 of the needle 60.

With this arrangement, air in the catheter 50, and in particular the interior 28 of the balloon 14, may be vented or purged as discussed previously. Once air has been removed from the catheter 50, the needle 60 may be slowly removed from the resealable material 58. As the needle 60 is removed from the resealable material 58, the vent lumen 54 is resealed, thus closing the vent pathway. Preferably, the needle 60 is partially withdrawn from the resealable material 58, and the resealable material is allowed to relax for approximately 15 seconds to fill the void left by the needle 60. If, after complete removal of the needle 60, fluid continues to flow through the resealable material 58, the needle 60 may be reinserted and withdrawn slowly again. After removal of the needle 60 without leakage, the occlusion catheter 50 is ready for use.

Refer now to FIGS. 16 and 17, which illustrate longitudinal cross-sectional views of a distal portion of occlusion balloon catheter 70 in accordance with a further embodiment of the present invention. Except as described herein, occlusion balloon catheter 70 may be the same in structure and use as occlusion catheter 10 described with reference to FIGS. 1-6 and occlusion catheter 30 or 50 described with reference to FIGS. 7-13 and FIGS. 14-15, respectively. Occlusion balloon catheter 70 includes an intermediate tube 71 disposed between the elongate shaft 12 and the occlusion balloon 14. Intermediate tube 71 includes an inner tube 76 disposed inside an outer tube 74. The inner tube 76 of the intermediate tube 71 includes an inflation lumen 72 providing a fluid connection between the inflation lumen 26 of the shaft 12 and the interior 28 of the balloon 14.

A resealable material 78 is disposed in the annular lumen defined between the inner tube 76 and the outer tube 74. The resealable material 78 operates essentially the same as the resealable material 58 described with reference to FIGS. 14 and 15. However, the needle 60 is inserted laterally through the intermediate tube 71, piercing the outer tube 74 and the inner tube 76. The resealable material 78 serves to seal the void defined by the needle 60 when inserted into the intermediate tube 71.

With this arrangement, a vent pathway is defined from the interior 28 of the balloon 14, through the lumen 72 of the intermediate tube 71, and into the lumen 62 of the needle 60. Once air has been purged from the catheter 70, and in particular the interior 28 of the balloon 14, the needle 60 may be slowly removed from the intermediate tube 71, such that the resealable material 78 is allowed to fill the void left by the needle 60 and thereby close the vent pathway. After removal of the needle 60 and closure of the vent pathway, the occlusion catheter 70 is ready for use.

Refer now to FIGS. 18, 19, and 20, which illustrate a distal portion of an occlusion catheter 120 in accordance with a further embodiment of the present invention. Except as noted herein, occlusion balloon catheter 120 is the same in structure and use as the occlusion catheters previously described. Occlusion balloon catheter 120 includes an intermediate tube or sleeve 122 coaxially disposed about catheter shaft 12. Intermediate tube 122 is illustrated in a first, open position in FIG. 18. Inflation lumen 26 narrows to a distal inflation lumen portion 126 defined by distal inflation tube walls 128 terminating in a distal inflation tube port 130 leading into balloon interior 28. Balloon interior 28 is in fluid communication with a vent lumen 132 defined between inflation tube walls 128 and a vent tube wall 134. Vent lumen 132 curves from a longitudinal orientation to an angle relative to the wall of shaft 12, and terminates proximally in a vent hole 136. A first seal or gasket 138 is disposed distal of vent hole 136. A second seal or gasket 140 is disposed proximal of vent hole 136. Seals 138 and 140 are preferably annular seals which surround shaft 12. Seals 138 and 140 can be formed of materials such as silicone rubber and can be formed as O-rings in some embodiments.

FIG. 19 illustrates occlusion catheter 120 in a second, closed and sealed position. Intermediate tube or sleeve 122 is illustrated in a sealed position, having the inner wall of sleeve 122 in contact with both distal seals 138 and proximal seals 140, thereby forming a seal over vent hole 136. FIG. 20 is a transverse cross-sectional view of shaft 12 through a portion having both lumen 126 and vent lumen 132. In one embodiment, the dual lumen portion is formed as a single extrusion. In another embodiment, the dual lumen portion is formed by necking down lumen 26 to 126 and securing a second vent tube having vent lumen 132 to the top of the necked down shaft.

In use, occlusion catheter 120 can be put into the first, open position illustrated in FIG. 18 by having sleeve 122 slid into the proximal position as illustrated. In another embodiment, not requiring illustration, sleeve 122 can be disposed distally of vent hole 136 while in the open position, rather than proximally of vent hole 136. Liquid fluid can be injected into lumen 26, thereby flushing balloon interior 28, flowing through vent lumen 132, and exiting through vent hole 136. After balloon interior 28 has been flushed for a suitable period of time, and most or all of any gaseous fluid originally within balloon interior 28 purged, sleeve 122 can be slid into the second position illustrated in FIG. 19. Once in the closed position, inflation fluid can be supplied to inflate balloon 14.

Referring now to FIGS. 21 and 22, an occlusion catheter 142 is illustrated including a proximal tube 144 secured to an intermediate disposed tube 146, which is in turn secured to a distally disposed tube 148 having a distal opening 149. In a preferred embodiment, proximal tube 144 is formed of a polymeric material, intermediate tube 146 is formed of hypotube, and distal tube 148 is formed of a polymeric material. In one embodiment, tubes 144, 146, and 148 are formed of progressively more flexible material. A second, vent tube 152 is illustrated secured to distal tube 148. Vent tube 152 includes a vent lumen 150 therein. Vent lumen 150 terminates proximally in a vent hole 154. In FIG. 21, vent hole 154 has an inner diameter slightly less than the inner diameter of lumen 150. While in the open position illustrated in FIG. 21, fluid can be forced through lumen 26, thereby flushing balloon interior 28, and exiting through vent lumen 150 and vent hole 154.

Referring now to FIG. 22, occlusion catheter 142 is illustrated in a closed or sealed position. A sealing plug 156 is illustrated, occluding vent lumen 150. In a preferred embodiment, sealing plug 156 includes a radiopaque material so as to be visible under fluoroscopy. Plug 156 can be formed of an elastic material such as medical grade silicon rubber. In an alternate embodiment, plug 156 is formed in place with a rapidly curing polymeric material injected into vent lumen 150. Plug 156 can be inserted in place using a mandrel when the purging of balloon interior 28 is complete. With plug 156 in place, occlusion device balloon 14 can be inflated as illustrated in FIG. 22.

Figure 23:
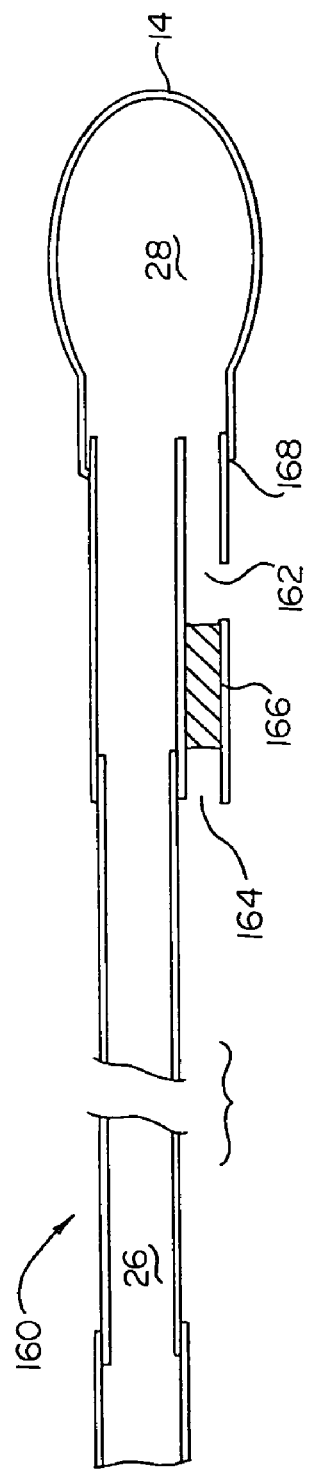
FIG. 23 is a partial longitudinal cross-sectional view of an occlusion balloon catheter including a distal purge lumen having a slidable proximally disposed plug, a proximal plug access port, and an intermediate disposed exit port.
Figure 24:
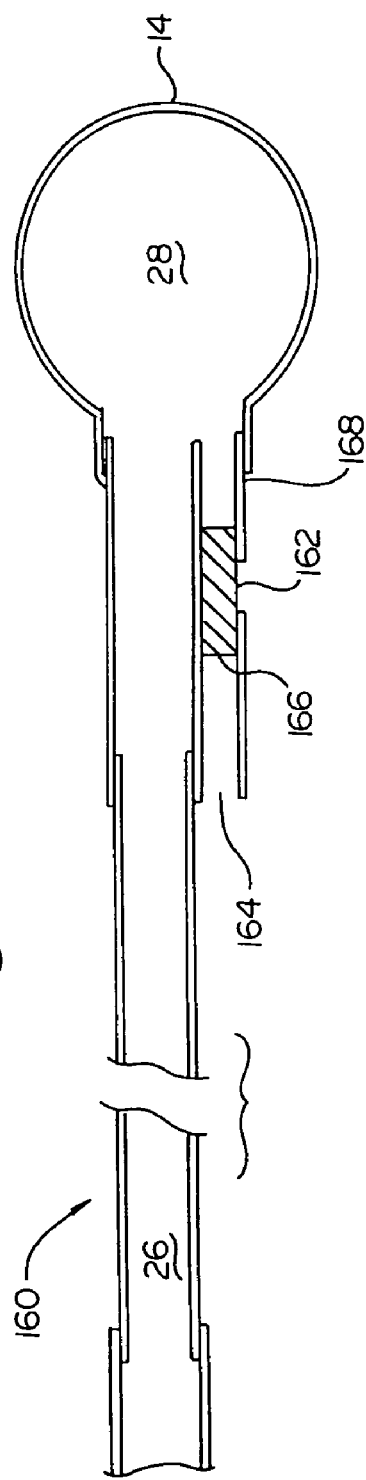
FIG. 24 is a partial longitudinal cross-sectional view of the occlusion balloon catheter illustrated in FIG. 23 and having the plug blocking the exit port.

Referring now to FIGS. 23 and 24, a distal portion of an occlusion device 160 is illustrated having features similar to device 142 illustrated in FIGS. 21 and 22. Occlusion device 160 includes a vent tube 168 having a proximal plug access port 164 and an intermediate disposed vent hole 162 in the side wall of vent tube 168. FIG. 23 illustrates device 160 in open position, allowing purge fluid to flow through lumen 26, into balloon interior 28, through vent tube 168, and out vent hole 162. In the open position, a slidable plug 166 is disposed in vent tube 168 proximal of vent hole 162. FIG. 24 illustrates device 160 in a closed or sealed position. In the sealed position, plug 166 has been slid distally so as to occlude vent hole 162. Plug 166 can be pushed distally from the plug open position by inserting a push rod through plug access hole 164.

Refer now to FIG. 25, which illustrates a longitudinal cross-sectional view of a removable hub 100 for use in combination with any of the catheters 10, 30, 50, and 70 described herein. Removable hub 100 is releasably secured to the proximal end of the shaft 12 to facilitate connection to a fluid source (not shown), such as a fluid-filled syringe or an inflation device. As illustrated, removable hub 100 utilizes a compression fitting, but those skilled in the art will recognize that other suitable mechanisms may be utilized to provide a fluid-tight, removable mechanical connection to the proximal end of the shaft 12.

Removable hub 100 includes a proximal portion 102 and a distal portion 104 connected by threaded portions 106. Proximal portion 102 may be rotated relative to distal portion 104 to compress or release an O-ring 110 disposed between the proximal portion 102 and the distal portion 104. When compressed, the O-ring 110 forms a fluid-tight seal with the elongate shaft 12. When released, the O-ring is radially displaced from the shaft 12, such that the hub 100 may be removed therefrom. The elongate shaft 12 may include a retainer ring 13 to assist in the mechanical engagement between the removable hub 100 and the shaft 12. The proximal end 102 of the hub 100 includes a standard fitting 108 for connection to a fluid source. The removable hub 100 may be used as discussed with reference to FIGS. 1-4.

Those skilled in the art will recognize that the present invention may be manifested in a wide variety of forms other than the specific embodiments contemplated and described herein. Accordingly, departures in form and detail may be made without departing from the scope or spirit of the present invention as described in the appended claims.

Numerous advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The invention's scope is, of course, defined in the language in which the appended claims are expressed.

What is claimed is:

1. An intravascular occlusion balloon catheter, comprising:
   an elongate tubular shaft having a hub end and a balloon end, wherein the hub end is the end that normally remains outside a human body and the balloon end is the end of the shaft that extends furthest into the human body;
   a removable hub connected to the hub end of the shaft;
   an inflatable occlusion balloon disposed near the balloon end of the shaft; and
   means for selectively venting air from the balloon, the means disposed between the balloon and the hub end of the shaft.

2. An intravascular occlusion balloon catheter as in claim 1, wherein the venting means comprises:
   an annular ring disposed about the balloon end of the shaft; and
   an intermediate tube fixedly attached to the balloon and movably disposed about the annular ring, the intermediate tube and the annular ring forming a seal, the intermediate tube having a vent hole, wherein a vent path is opened through the intermediate tube and the vent hole when the hole is positioned on the side of the annular ring closest to the balloon end of the shaft, and the vent path is closed when the vent hole is positioned on the side of the annular ring closest to the hub end of the shaft.

3. An intravascular occlusion balloon catheter as in claim 1, wherein the venting means comprises:
   an intermediate tube disposed between the balloon and the balloon end of the shaft, the tube having an inflation lumen and a vent lumen; and
   a re-sealable material disposed in the vent lumen, wherein a vent path is opened when a needle is disposed through the re-sealable material, and the vent path is closed when the needle is removed from the re-sealable material.

4. An intravascular occlusion balloon catheter as in claim 3, wherein the intermediate tube comprises a side-by-side dual lumen tube.

5. An intravascular occlusion balloon catheter as in claim 3, wherein the intermediate tube comprises an inner tube coaxially disposed in an outer tube and the vent lumen comprises an annular lumen therebetween.

6. An intravascular occlusion balloon catheter as in claim 1, wherein the venting means comprises:
   a vent lumen extending from the balloon to a vent port; and
   a sleeve slidably and coaxially disposed near the shaft balloon end, the sleeve having a first position for occluding the vent port and a second position for allowing airflow from the vent port.

7. An intravascular occlusion balloon catheter as in claim 6, wherein the sleeve has a length, the venting means further comprising a first seal disposed on the side of the vent port closest to the hub end of the shaft and a second seal disposed on the side of the vent port closest to the balloon end of the shaft, the first and second seals disposed a distance apart less than the sleeve length, the first and second seals having a height sufficiently small to fit between the sleeve and the shaft when the sleeve is in the first position.

8. An intravascular occlusion balloon catheter, comprising:
   an elongate tubular shaft having a hub end and a balloon end, wherein the hub end is the end that normally remains outside a human body and the balloon end is the end of the shaft that extends furthest into the human body;
   a removable hub connected to the hub end of the shaft;
   an inflatable occlusion balloon disposed near the balloon end of the shaft, the balloon having an interior; and
   a vent pathway disposed on the balloon end of the shaft, the vent pathway in fluid communication with the interior of the balloon for selectively venting air from the balloon, and the vent pathway disposed between the balloon and the hub end of the shaft.

9. An intravascular occlusion balloon catheter as in claim 8, further comprising:
   an annular ring disposed about the balloon end of the shaft; and
   an intermediate tube fixedly connected to the balloon and movably disposed about the annular ring, the intermediate tube forming a seal with the annular ring, the intermediate tube having a vent hole therein, wherein the vent pathway is defined from the interior of the balloon, between the intermediate tube and the shaft to the annular ring, and through the vent hole; and
   wherein the vent pathway is open when the vent hole is positioned on the side of the annular ring closest to the balloon end of the shaft and the vent pathway is closed when the vent hole is positioned on the side of the annular rind closest to the hub end of the shaft.

10. An intravascular occlusion balloon catheter as in claim 8, further comprising:
    an intermediate tube disposed between the balloon and the balloon end of the shaft, the tube having an inflation lumen and a vent lumen; and
    a re-sealable material disposed in the vent lumen, wherein the vent pathway is defined from the interior of the balloon and through a removable needle disposed in the re-sealable material, and wherein the vent pathway is opened when a needle is disposed through the re-sealable material, and the vent pathway is closed when the needle is removed from the re-sealable material.

11. An intravascular occlusion balloon catheter as in claim 10, wherein the intermediate tube comprises a side-by-side dual lumen tube.

12. An intravascular occlusion balloon catheter as in claim 10, wherein the intermediate tube comprises an inner tube coaxially disposed in an outer tube and the vent lumen comprises an annular lumen therebetween.

13. An intravascular occlusion balloon catheter as in claim 8, further comprising a sleeve slidably and coaxially disposed near the shaft balloon end, wherein the vent pathway extends from the balloon through a vent lumen and through a vent port, the sleeve having a first position for occluding the vent pathway and a second position for allowing airflow through the vent pathway.

14. An intravascular occlusion balloon catheter as in claim 13, wherein the sleeve has a length, further comprising a first seal disposed on the side of the vent port closest to the hub end of the shaft and a second seal disposed on the side of the vent port closest to the balloon end of the shaft, the first and second seals disposed a distance apart less than the sleeve length, the first and second seals having a height sufficiently small to fit between the sleeve and the shaft when the sleeve is in the first position.

15. An intravascular occlusion balloon catheter, comprising:
 an elongate tubular shaft having a proximal end and a distal end;
 a removable hub connected to the proximal end of the shaft;
 an inflatable occlusion balloon disposed near the distal end of the shaft, the balloon having an interior; and
 a vent pathway disposed on the distal end of the shaft proximal the balloon, the vent pathway in fluid communication with the interior of the balloon for selectively venting air from the balloon.

16. An intravascular occlusion balloon catheter as in claim 15, further comprising:
 an annular ring disposed about the distal end of the shaft; and
 an intermediate tube fixedly connected to the balloon and movably disposed about the annular ring, the intermediate tube forming a seal with the annular ring, the intermediate tube having a vent hole therein, wherein the vent pathway is defined from the interior of the balloon, between the intermediate tube and the shaft to the annular ring, and through the vent hole; and
 wherein the vent pathway is open when the vent hole is positioned on the distal side of the annular ring and the vent pathway is closed when the vent hole is positioned on the proximal side of the annular ring.

17. An intravascular occlusion balloon catheter as in claim 15, further comprising:
 an intermediate tube disposed between the balloon and the distal end of the shaft, the tube having an inflation lumen and a vent lumen; and
 a re-sealable material disposed in the vent lumen, wherein the vent pathway is defined from the interior of the balloon and through a removable needle disposed in the re-sealable material, wherein the vent pathway is opened when a needle is disposed through the re-sealable material, and the vent path is closed when the needle is removed from the re-sealable material.

18. An intravascular occlusion balloon catheter as in claim 17, wherein the intermediate tube comprises a side-by-side dual lumen tube.

19. An intravascular occlusion balloon catheter as in claim 17, wherein the intermediate tube comprises an inner tube coaxially disposed in an outer tube and the vent lumen comprises an annular lumen therebetween.

20. An intravascular occlusion balloon catheter as in claim 15, further comprising a sleeve slidably and coaxially disposed near the shaft distal end, wherein the vent pathway extends from the balloon through a vent lumen and through a vent port, the sleeve having a first position for occluding the vent pathway and a second position for allowing airflow through the vent pathway.

21. An intravascular occlusion balloon catheter as in claim 20, wherein the sleeve has a length, further comprising a first seal disposed proximal of the vent port and a second seal disposed distal of the vent port, the first and second seals disposed a distance apart less than the sleeve length, the first and second seals having a height sufficiently small to fit between the sleeve and the shaft when the sleeve is in the first position.

* * * * *

UNITED STATES PATENT AND TRADEMARK OFFICE
CERTIFICATE OF CORRECTION

PATENT NO. : 7,641,669 B2 Page 1 of 1
APPLICATION NO. : 10/811609
DATED : January 5, 2010
INVENTOR(S) : Roychowdhury et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1682 days.

Signed and Sealed this

Sixteenth Day of November, 2010

David J. Kappos
*Director of the United States Patent and Trademark Office*